United States Patent
Han et al.

(10) Patent No.: US 12,376,807 B2
(45) Date of Patent: Aug. 5, 2025

(54) COLLIMATOR FOR DENTAL X-RAY IMAGING APPARATUS

(71) Applicant: Fangkai Han, Shanghai (CN)

(72) Inventors: Fangkai Han, Shanghai (CN); Jue Li, Shanghai (CN)

(73) Assignee: Fangkai Han, Shanghai (CN)

( * ) Notice: Subject to any disclaimer, the term of this patent is extended or adjusted under 35 U.S.C. 154(b) by 340 days.

(21) Appl. No.: 18/114,801

(22) Filed: Feb. 27, 2023

(65) Prior Publication Data

US 2023/0277143 A1  Sep. 7, 2023

Related U.S. Application Data (63) Continuation-in-part of application No. PCT/CN2020/134207, filed on Dec. 7, 2020.

(30) Foreign Application Priority Data

Aug. 31, 2020  (CN) .......... 202010897300.X
Aug. 31, 2020  (CN) .......... 202010899150.6

(51) Int. Cl.
  *A61B 6/14*  (2006.01)
  *A61B 6/06*  (2006.01)
  (Continued)

(52) U.S. Cl.
  CPC .......... *A61B 6/06* (2013.01); *A61B 6/08* (2013.01); *A61B 6/51* (2024.01)

(58) Field of Classification Search
  CPC .. A61B 6/50; A61B 6/512; A61B 6/44; A61B 6/4411; A61B 6/4435; A61B 6/447;
  (Continued)

(56) References Cited

U.S. PATENT DOCUMENTS

RE46,463 E  7/2017  Fienbloom et al.
2008/0298543 A1*  12/2008  Razzano .......... A61B 6/563
                                                      378/170
(Continued)

FOREIGN PATENT DOCUMENTS

CN  105078485 A  11/2015
CN  205514657 U  8/2016
(Continued)

OTHER PUBLICATIONS

Decision of Rejection, CN202010899150.6, Mar. 14, 2024, 8 pages; English Translation, 5 pages.
(Continued)

*Primary Examiner* — Don K Wong
(74) *Attorney, Agent, or Firm* — BLANK ROME LLP (57) ABSTRACT

A collimator for a dental X-ray imaging apparatus, including: a housing (3) having a first end and a second end, which oppose each other, the first end provided thereat with a light exit aperture, the second end secured to the dental X-ray imaging apparatus so as to define a light passage so that X-rays are able to travel through the light passage and exit from the light exit aperture; a securing means disposed at the second end, with which the housing (3) is detachably secured to a beam-limiting cone (10); a visible light source (12) placed within the housing (3) and configured to be able to emit visible light; a window member disposed at the first end of the housing and configured to allow visible light and X-rays to transmit therethrough and be projected and irradiated onto an object to be imaged; a light-reflecting plate (13) placed in the housing (3) obliquely with respect to a longitudinal axis of the light passage and configured to be able to reflect visible light emitted from the visible light source (12) so that it is able to pass through the window member and be projected on the object to be imaged; a beam-limiting member disposed between the light-reflecting (Continued)

plate (13) and the window member and configured to disallow transmission of visible light and X-rays therethrough and hence define the light exit aperture.

20 Claims, 8 Drawing Sheets

(51) Int. Cl.
    *A61B 6/08*     (2006.01)
    *A61B 6/51*     (2024.01)

(58) Field of Classification Search
    CPC ....... A61B 6/08; A61B 5/0059; A61B 5/0077;
           A61B 5/0079; A61B 5/0082; A61B
           5/0088; G03B 42/02; G03B 42/042;
             G03B 42/045; G03B 42/047
    See application file for complete search history.

(56) References Cited

U.S. PATENT DOCUMENTS

| | | |
|---|---|---|
| 2013/0136238 A1 | 5/2013 | Laws et al. |
| 2014/0126687 A1 | 5/2014 | Yoshikawa et al. |
| 2016/0135767 A1 | 5/2016 | Kim |
| 2018/0263578 A1 | 9/2018 | Abramovich et al. |

FOREIGN PATENT DOCUMENTS

| | | |
|---|---|---|
| CN | 207148015 U | 3/2018 |
| CN | 103453330 A | 12/2018 |
| CN | 208889601 U | 5/2019 |
| CN | 110602993 A | 12/2019 |
| CN | 209895780 U | 1/2020 |
| CN | 111568461 A | 8/2020 |
| CN | 111870271 A | 11/2020 |
| CN | 111870272 A | 11/2020 |
| WO | WO-2013/127005 A1 | 9/2013 |

OTHER PUBLICATIONS

Decision of Rejection, CN202010897300.X, Mar. 15, 2024, 16 pages; English Translation, 19 pages.
International Search Report for PCT/CN2020/134207, dated May 31, 2021, 5 pgs.

* cited by examiner

COLLIMATOR FOR DENTAL X-RAY IMAGING APPARATUS

RELATED APPLICATIONS

This application is a continuation-in-part (CIP) application claiming benefit of PCT/CN2020/134207 filed on Dec. 7, 2020, which claims priority to Chinese Patent Application No. 202010899150.6 filed on Aug. 31, 2020 and Chinese Patent Application No. 202010897300.X filed on Aug. 31, 2020, the disclosures of which are incorporated herein in their entirety by reference.

FIELD OF THE INVENTION

The present disclosure relates to the field of oral and maxillofacial imaging technology and, in particular, to a collimator for a dental X-ray imaging apparatus and a method of using it.

DESCRIPTION OF THE PRIOR ART

Collimators are commonly used in imaging equipment used in medical physical examinations, such as X-ray imaging equipment for chest and extremity examinations. As the name suggests, a collimator acts to collimate a light beam. In practice, a light on a collimator is first turned on, and rotary switches on the collimator for adjustment in two mutually perpendicular directions are then tuned to cause visible light from the collimator to be irradiated onto a film cassette so that a visible light field or light field produced is just as big as a film in the cassette. When this is achieved, it is considered suitable to commence an X-ray imaging process.

Minimizing a deviation between the X-ray and visible light fields can enable the light field to represent the invisible X-ray field. However, this remains unachieved in the field of oral and maxillofacial imaging, in particular dental X-ray imaging that is most widely used in clinical practice.

There are two conventional techniques for this purpose, one of which is the bisecting-angle technique most commonly used in clinical practice. This technique is theoretically established, but it suffers from non-perpendicularity of a central X-ray in a projected X-ray beam with respect to a long axis of a tooth and a film (imaging plate) to be imaged because it relies on an imaginary bisecting-angle line for orientation adjustment of the central X-ray. This is, however, usually inaccurate, often leading to distortion of a captured tooth image. The major problem with this technique is that the position of such a bisecting-angle line is ambiguous and undetectable. Regarding the projection direction and the alignment with a target site, textbooks and standards in the health industry recommend taking a patient's facial soft tissue landmarks as reference points. Obviously, using such landmarks as reference points for dental X-ray imaging is associated with too much doubt and uncertainty. It is also specified that a central X-ray should be parallel to a tangent to an adjacent aspect of a tooth under examination as much as possible. The phrase "as much as possible" used here portrays the doubtfulness and impreciseness of this technique. Moreover, too much error tolerance is specified for this technique. The other conventional technique is paralleling, which can ensure perpendicularity of a central X-ray to the surface of a film, instead of relying on an imaginary bisecting-angle line for this purpose. However, this technique also suffers from the problem of frustrated implementation despite theoretical perfectness. In most cases, limited by the size of a patients' oral cavity, the position for an imaging plate where it can achieve theoretical parallelism of to a long axis of a tooth to be imaged is located outside the oral cavity. Therefore, although these two techniques seem reasonable in theory, their implementation suffers from too much uncertainty in terms of alignment with a target site.

Therefore, those skilled in the art are directing their effort toward developing a collimator for a dental X-ray imaging apparatus and method of using it, which can produce an optimal X-ray field with reduced radiation exposure, enable more accurate projection to a desired area, reduce unnecessary irradiation of areas not of interest and patient dose and enhance image quality.

SUMMARY OF THE INVENTION

In view of the above described drawbacks of the prior art, the problem sought to be solved by the present invention is to overcome the problem of unnecessary exposure to X-ray radiation of surrounding body tissues encompassed by a radiation field that is much larger than an area of interest during dental imaging.

In order to achieve the above goal, in a first aspect of the present invention, there is provided a collimator for a dental X-ray imaging apparatus, including: a housing having a first end and a second end, which oppose each other, the first end of the housing provided thereat with a light exit aperture, the second end of the housing secured to the dental X-ray imaging apparatus so as to define a light passage so that X-rays emitted from the dental X-ray imaging apparatus are able to travel through the light passage and exit from the light exit aperture; a securing means disposed at the second end of the housing, with which the housing is detachably secured to a beam-limiting cone in the dental X-ray imaging apparatus; a visible light source placed within the housing and configured to be able to emit visible light; a window member disposed at the first end of the housing and configured to allow visible light and X-rays to transmit therethrough and be projected and irradiated onto an object to be imaged; a light-reflecting plate placed in the housing obliquely with respect to a longitudinal axis of the light passage and configured to be able to reflect visible light emitted from the visible light source so that the reflected visible light is able to pass through the window member and be projected on the object to be imaged; a beam-limiting member disposed between the light-reflecting plate and the window member and configured to disallow transmission of visible light and X-rays therethrough and hence define the light exit aperture.

Further, the visible light source is positioned on an inner wall of the housing.

Further, the window member is provided at a center thereof with a light-shading mark for indicating an area on which the visible light is projected.

Further, the light-reflecting plate is made of a material transmissive to X-rays.

Further, the light-reflecting plate forms an angle of 45° with the longitudinal axis of the light passage.

Further, a position of a virtual image of the visible light source formed by the light-reflecting plate coincides with a position of an X-ray source in the dental x-ray imaging apparatus in a direction along the longitudinal axis of the light passage.

Further, the collimator additionally includes an adjustment member disposed on the housing and configured to be able to change a size and/or a shape of the light exit aperture defined by the beam-limiting member.

Further, the visible light source is an LED lamp.

Further, the securing means is configured to be able to be fitted over and thereby connected to an outer circumference of the beam-limiting cone in the dental X-ray imaging apparatus.

Further, the securing means is configured to be able to be connected to a bottom of the beam-limiting cone in the dental X-ray imaging apparatus by magnetic attraction.

Further, the beam-limiting member further includes a set of first beam-limiting blocks and a set of second beam-limiting blocks, which are arranged orthogonally to each other, the set of first beam-limiting blocks including a pair of first beam-limiting blocks in opposition to each other, and the set of second beam-limiting blocks including a pair of second beam-limiting blocks in opposition to each other, wherein the adjustment member is configured to control the pair of first beam-limiting blocks to move relative to each other and to control the pair of second beam-limiting blocks to move relative to each other.

Further, the beam-limiting member further includes a stationary portion and a movable portion, the stationary portion configured as an annulus, the movable portion comprising a plurality of beam-limiting blocks, each of the plurality of beam-limiting blocks pivotably coupled to the stationary portion and evenly distributed around a center of the stationary portion, wherein the adjustment member is configured to switch the plurality of beam-limiting blocks between a closed state and an open state.

Further, the housing is additionally provided thereon with a switch for activating or deactivating the visible light source.

Further, the housing is additionally provided thereon with an infrared sensing device configured to sense the object to be imaged and responsively activate or deactivate the visible light source.

In another aspect of the present invention, there is provided a dental X-ray imaging apparatus, including: an X-ray source; a body for housing the X-ray source; a beam-limiting cone disposed externally around the X-ray source and extending out of the body; a collimator comprising: a housing having a first end and a second end, which oppose each other, the first end of the housing provided thereat with a light exit aperture, the second end of the housing secured to the beam-limiting cone so as to define a light passage so that X-rays emitted from the dental X-ray imaging apparatus are able to travel through the light passage and exit from the light exit aperture; a securing means disposed at the second end of the housing, with which the housing is detachably secured to the beam-limiting cone; a visible light source placed within the housing and configured to be able to emit visible light; a window member disposed at the first end of the housing and configured to allow visible light and X-rays to transmit therethrough and be projected and irradiated onto an object to be imaged; a light-reflecting plate placed in the housing obliquely with respect to a longitudinal axis of the light passage and configured to be able to reflect visible light emitted from the visible light source so that the reflected visible light is able to pass through the window member and be projected on the object to be imaged; a beam-limiting member disposed between the light-reflecting plate and the window member and configured to disallow transmission of visible light and X-rays therethrough and hence define the light exit aperture.

Further, the visible light source is positioned on an inner wall of the housing.

Further, the window member is provided at a center thereof with a light-shading mark for indicating an area on which the visible light is projected.

Further, the light-reflecting plate is made of a material transmissive to X-rays.

Further, the light-reflecting plate forms an angle of 45° with the longitudinal axis of the light passage.

Further, a position of a virtual image of the visible light source formed by the light-reflecting plate coincides with a position of the X-ray source in the dental x-ray imaging apparatus in a direction along the longitudinal axis of the light passage.

Further, the collimator additionally includes an adjustment member disposed on the housing and configured to be able to change a size and/or a shape of the light exit aperture defined by the beam-limiting member.

Further, the beam-limiting member further includes a set of first beam-limiting blocks and a set of second beam-limiting blocks, which are arranged orthogonally to each other, the set of first beam-limiting blocks including a pair of first beam-limiting blocks in opposition to each other, and the set of second beam-limiting blocks including a pair of second beam-limiting blocks in opposition to each other, wherein the adjustment member is configured to control the pair of first beam-limiting blocks to move relative to each other and to control the pair of second beam-limiting blocks to move relative to each other.

Further, the beam-limiting member further includes a stationary portion and a movable portion, the stationary portion configured as an annulus, the movable portion comprising a plurality of beam-limiting blocks, each of the plurality of beam-limiting blocks pivotably coupled to the stationary portion and evenly distributed around a center of the stationary portion, wherein the adjustment member is configured to switch the plurality of beam-limiting blocks between a closed state and an open state.

Further, the housing is additionally provided thereon with an infrared sensing device configured to sense the object to be imaged and responsively activate or deactivate the visible light source.

In yet another aspect of the present invention, there is provided a method of using a collimator for a dental X-ray imaging apparatus, including the steps of:
- affixing the collimator to a beam-limiting cone in the dental X-ray imaging apparatus; causing visible light emitted from a visible light source to be projected through a window member;
- adjusting a distance and orientation of the beam-limiting cone in the dental X-ray imaging apparatus from and with respect to an object to be imaged;
- adjusting a beam-limiting member to change a shape and size of a light field produced by the projected visible light;
- determining area for dental imaging and a projection direction for X-rays based on the light field produced by the visible light from the window member; and activating the dental X-ray imaging apparatus and performing X-ray exposure.

In still yet another aspect of the present invention, there is provided a method of using a dental X-ray imaging apparatus, including the steps of:
- causing visible light emitted from a visible light source to be projected through a window member;
- adjusting a distance and orientation of a beam-limiting cone in the dental X-ray imaging apparatus from and with respect to an object to be imaged;

adjusting a beam-limiting member to change a shape and size of a light field produced by the projected visible light;

determining area for dental imaging and a projection direction for X-rays based on the light field produced by the visible light from the window member; and activating the dental X-ray imaging apparatus and performing X-ray exposure.

To the knowledge of the inventors, a beam-limiting cone of a dental imaging apparatus is required to have a length not less than 20 cm, an effective beam diameter at the exit end of not more than 7 cm and a wall providing protection equivalent to that provided by at least 0.5 mm of lead. These requirements are of great significance to limiting the extent of a radiation field and reducing stray X-rays from the radiation field, and highlight the importance of radiation field limitation. According to the present invention, guided by an indication provided by visible light, the collimator can be effectively adjusted to block and filter X-rays to limit an X-ray radiation field to be produced, avoiding unnecessary exposure. Therefore, it complies with the internationally accepted principles of radiation dose optimization and is capable of effectively limiting X-rays in the dental imaging apparatus and locating and determining an X-ray radiation field under the guidance of visible light, enabling the establishment of a more accurate projection system.

The present invention has the following benefits:

1) The collimator enables integration and synchronized adjustment of visible light and X-ray fields and allows a radiation field and its size to be adjusted. Moreover, it is capable of accurate projection and allows easy operation.

2) Compared with the prior art, it significantly reduces repeated failed imaging attempts. This makes it more compliant with the principles of radiation dose optimization and effectively reduces a patient's unnecessary exposure to radiation due to such repeated failed imaging attempts. Moreover, it provides enhanced image quality.

3) Its visualization ability rationally supplements the conventional projection techniques for dental imaging apparatuses and improves the theoretical system of projection technology for periapical imaging in oral and maxillofacial radiography.

Below, the concept, structural details and resulting technical effects of the present application will be further described with reference to the accompanying drawings to provide a full understanding of the objects, features and effects of the invention.

BRIEF DESCRIPTION OF THE DRAWING

FIG. 16 is a schematic diagram illustrating the structure of a collimation casing in an internally-disposed circular collimator for a dental X-ray imaging apparatus according to the present application, in which 1 denotes an up-down light field adjustment rotary switch; 2, a left-right light field adjustment rotary switch; 3, a housing; 4, securing ring; 5, a rotary screw; 6, a screw; 7, a light field viewing window; 8, a crosshair; 9, an infrared sensing region; 10, a beam-limiting cone in a dental imaging apparatus; 11, an X-ray source; 12, a visible light source; 13, a light-reflecting plate; 14, a beam-limiting plate; 15, a light field adjusting lever; 16, a light projection casing; 17, a light source switch; 18, a transparent cover; 19, a collimation casing; 10—infrared sensing region; 20, a magnetically attractive member; 21, a projection target plate; and 22, a light field created by projected light.

DETAILED DESCRIPTION OF THE PREFERRED EMBODIMENTS

Below, the accompanying drawings of this specification are referenced to introduce many preferred embodiments of the present invention so that the techniques thereof become more apparent and readily understood. This invention may be embodied in many different forms of embodiment, and the protection scope thereof is not limited only to the embodiments mentioned herein.

Throughout the accompanying drawings, structurally identical parts are indicated with identical reference numerals, and structurally or functionally similar components are indicated with similar reference numerals. The size and thickness of each component in the drawings are arbitrarily depicted, and the present invention is not limited to any size or thickness of each component. For greater clarity of illustration, the thicknesses of some parts are exaggerated as appropriate somewhere in the drawings.

The present disclosure relates to a collimator for a dental X-ray imaging apparatus for use in periapical imaging. A visible light field is produced in advance as a representation of an X-ray field, based on which the size and extent of the X-ray field can be adjusted.

A dental x-ray imaging apparatus takes an image using X-rays irradiated on a patient's face, which then travel though tissues such as gingivae and the alveolar bone and reach a specially made dental film that has been placed in the oral cavity. Such apparatuses feature low output power and a beam-limiting cone with a very small radiation field and high directivity allowing direct alignment with a target site to be examined. A dental x-ray imaging apparatus is usually equipped with an integrated projection head. After a patient has been positioned as desired, X-rays can be projected onto any intended tooth in a proper direction simply by moving the projection head. A dental X-ray imaging apparatus may also employ a hand-held body design, in which a projection head is integrated with a beam-limiting cone. This design is also capable of projecting X-rays onto any intended tooth in a proper direction.

The beam-limiting cone is a metal barrel in the shape of a circular cylinder or cone. Sometimes, it is lined with thin lead for enhanced shielding and protection against X-rays. During imaging, it relies mainly on the blockage and absorption of X-rays by a wall of the barrel to limit a radiation field. Therefore, the size of the radiation field may be determined by a length and a diameter of the beam-limiting cone. The radiation field is typically circular.

In some embodiments, the collimator is externally disposed on a beam-limiting cone in the dental X-ray imaging apparatus. In these cases, possible forms of the collimator include square and circular collimators. A square collimator is able to produce square or rectangular visible light and X-ray fields with an adjustable size. A circular collimator is able to produce circular visible light and X-ray field with an adjustable size. The adjustable sizes make the apparatus suitable to be used with films of various sizes. Embodiments of these two collimator forms will be described below.

Embodiment 1

Figure 1:
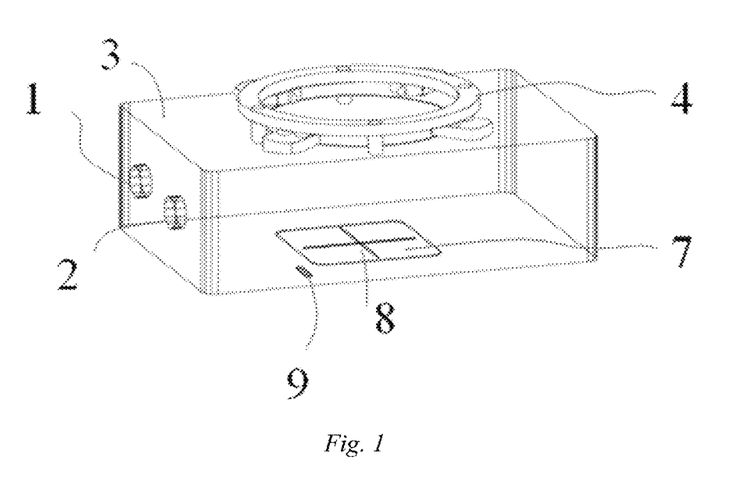
FIG. 1 is a schematic perspective view of the structure of an externally-disposed square collimator for a dental X-ray imaging apparatus according to the present application.

As shown in FIG. 1, an externally-disposed square collimator for a dental X-ray imaging apparatus includes a housing 3, a securing means, a visible light source 12 (see FIG. 4), a window member, a light-reflecting plate 13 (see FIGS. 3 and 4) and a beam-limiting member. In this embodiment, the securing means includes a securing ring 4 secured on one side of the housing 3, and the window member includes a light field viewing window 7 disposed on the housing 3 on the side thereof opposite to the securing ring 4 as a light exit aperture. As a result of the securing ring 4 being secured on said side of the housing 3 of the dental X-ray imaging apparatus, a light passage is formed, through which X-rays emitted from the dental X-ray imaging apparatus travel and exit from the light exit aperture. The light field viewing window 7 is made of a material allowing transmission of both visible light and X-rays therethrough. Additionally, a crosshair 8 is provided at the center of the light field viewing window 7 as a light-shading mark. As a result, when visible light exits the light field viewing window 7 and is projected onto a patient's face, a light field with a cross-shaped shadow indicating its center will be produced.

Figure 3:
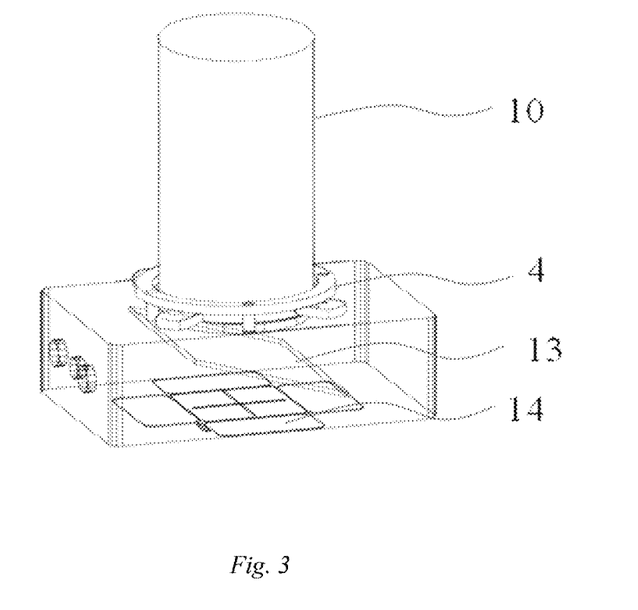
FIG. 3 is a schematic perspective view of the structure of an externally-disposed square collimator for a dental X-ray imaging apparatus according to the present application, which is fitted over an outer circumference of a beam-limiting cone in the dental imaging apparatus.

As shown in FIG. 3, the securing ring 4 is fitted over and secured to an outer circumference of the beam-limiting cone 10 in the dental imaging apparatus.

Figure 2:
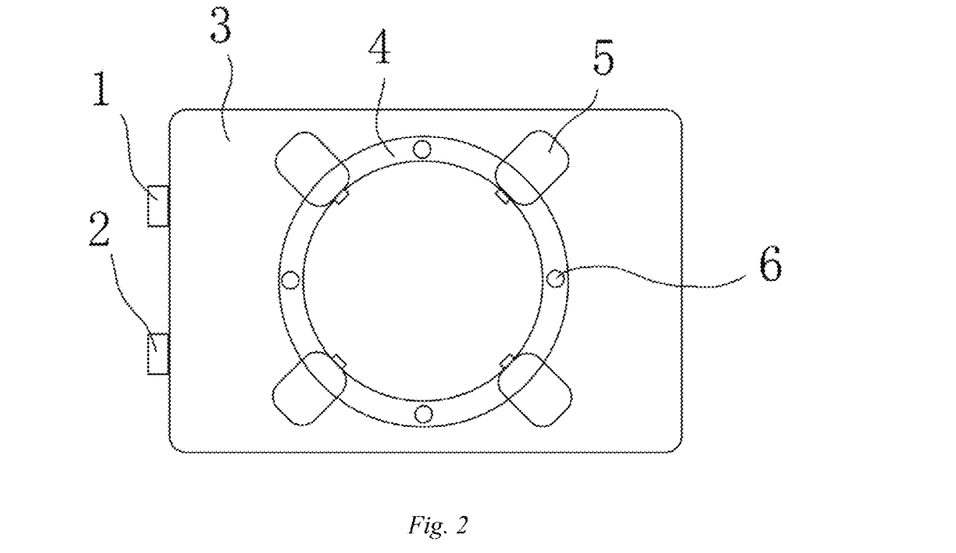
FIG. 2 is a top view of an externally-disposed square collimator for a dental X-ray imaging apparatus according to the present application.

In FIG. 2, the securing ring 4 is fitted over and secured by screws to the outer circumference of the beam-limiting cone 10 in the dental imaging apparatus. Rotary screws 5 may be tightened or loosened to secure the securing ring 4 to the outer circumference of the beam-limiting cone 10 in the dental imaging apparatus in a desired manner. The securing ring 4 is further secured to the housing 3 by tightening screws 6. Similarly, the securing ring 4 may be fitted over and secured alternatively by other fasteners or a circlip to the outer circumference of the beam-limiting cone 10 in the dental imaging apparatus. Still alternatively, it may be fitted over and secured by an elastic element (e.g., a rubber element) to the outer circumference of the beam-limiting cone 10 in the dental imaging apparatus.

Figure 4:
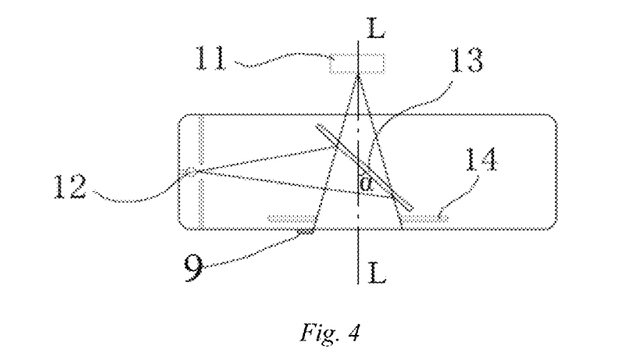
FIG. 4 schematically illustrates show an externally-disposed square collimator for a dental X-ray imaging apparatus according to the present application operates.

As shown in FIGS. 3 and 4, the visible light source 12 and the light-reflecting plate 13 are provided inside the housing 3 in such a manner that the light-reflecting plate 13 is inclined at an angle α of 45° with respect to a longitudinal axis L of the light passage (which is also a central axis of the housing 3) in order to reflect visible light emitted from the visible light source 12 toward the light field viewing window 7. The light-reflecting plate 13 is made of a material allowing transmission of X-rays therethrough. The visible light source 12 is an LED lamp, which is a cold light source generating less heat.

As shown in FIG. 1, as a means for adjusting the beam-limiting member, an up-down light field adjustment rotary switch 1 and a left-right light field adjustment rotary switch 2 are provided outside the housing 3. As shown in FIG. 3, the beam-limiting member includes beam-limiting plates 14 disposed within the housing 3 upstream of the light field viewing window 7. There are upper and lower beam-limiting plates 14 and left and right beam-limiting plates 14. The up-down light field adjustment rotary switch 1 is used to control movement of the upper and lower beam-limiting plates 14, and the left-right light field adjustment rotary switch 2 is used to control movement of the left and right beam-limiting plates 14.

Visible light and X-rays pass through the beam-limiting plates 14 and reach the light field viewing window 7. In use, the rotary switches may be manipulated as actually needed to control the size and extent of a light field produced. After passing through the light field viewing window 7, visible light will create a square or rectangular light field. The beam-limiting plates 14 are made of a material not allowing the transmission of visible light and X-rays therethrough.

As shown in FIG. 1, on the same side of the housing 3 as the light field viewing window 7, an infrared sensing device 9 is disposed. When a hand of a person or a part of an object is present in an infrared sensing region, infrared radiation emitted from an infrared transmitter will be reflected by the person's hand or body onto an infrared receiver. After processing, a signal is issued and received by the lamp and instructs the lamp to emit light. After the person's hand or the object leaves the infrared sensing region, the lamp will not receive any signal and therefore will not emit light. The infrared sensing region reaches 20 cm ahead, and the signal lasts for 30 seconds. After the signal disappears, another signal may be issued when another sensing event happens.

Embodiment 2

Figure 5:
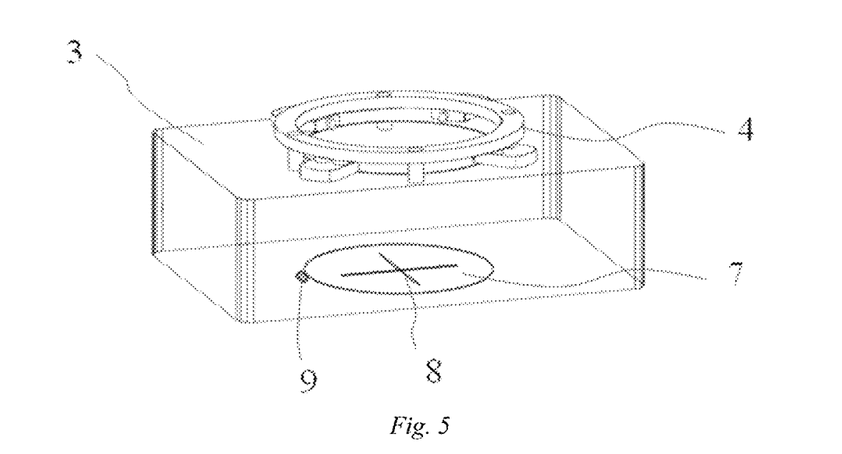
FIG. 5 is a schematic perspective view of the structure of an externally-disposed circular collimator for a dental X-ray imaging apparatus according to the present application.

As shown in FIG. 5, an externally-disposed circular collimator for a dental X-ray imaging apparatus includes a housing 3, a securing means, a visible light source 12 (see FIG. 4), a window member, a light-reflecting plate 13 (see FIG. 7) and a beam-limiting member. In this embodiment, the securing means includes a securing ring 4 secured on one side of the housing 3, and the window member includes a light field viewing window 7 disposed on the housing 3 on the side thereof opposite to the securing ring 4 as a light exit aperture. As a result of the securing ring 4 being secured on said side of the housing 3 of the dental X-ray imaging apparatus, a light passage is formed, through which X-rays emitted from the dental X-ray imaging apparatus travel and exit from the light exit aperture. The light field viewing window 7 is made of a material allowing transmission of both visible light and X-rays therethrough. Additionally, a crosshair 8 is provided at the center of the light field viewing window 7 as a light-shading mark. As a result, when visible light exits the light field viewing window 7 and is projected onto a patient's face, a light field with a cross-shaped shadow indicating its center will be produced.

Figure 7:
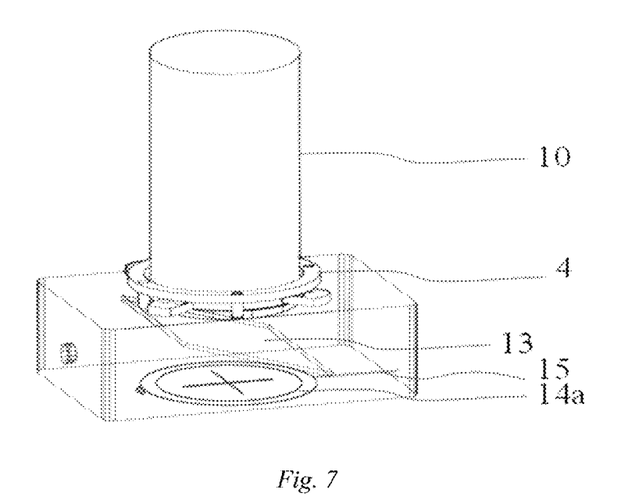
FIG. 7 is a schematic perspective view of the structure of an externally-disposed circular collimator for a dental X-ray imaging apparatus according to the present application, which is fitted over an outer circumference of a beam-limiting cone in the dental imaging apparatus.

As shown in FIG. 7, the securing ring 4 is fitted over and secured to an outer circumference of the beam-limiting cone 10 in the dental imaging apparatus.

Figure 6:
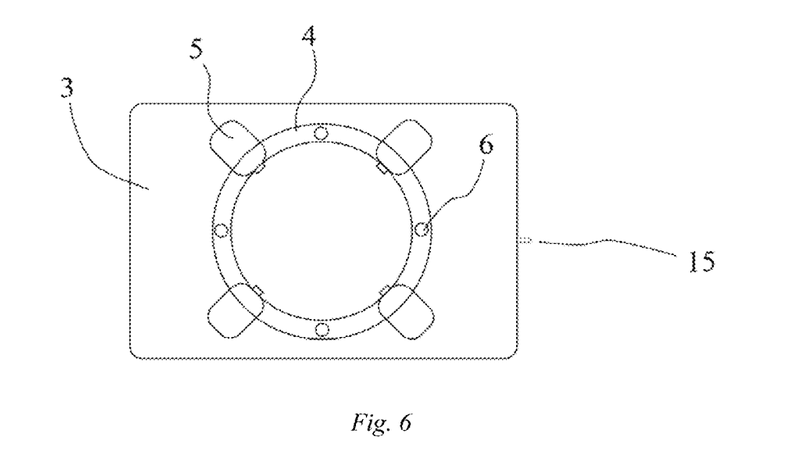
FIG. 6 is a top view of an externally-disposed circular collimator for a dental X-ray imaging apparatus according to the present application.

In FIG. 6, the securing ring 4 is fitted over and secured by screws to the outer circumference of the beam-limiting cone 10 in the dental imaging apparatus. Rotary screws 5 may be tightened or loosened to secure the securing ring 4 to the outer circumference of the beam-limiting cone 10 in the dental imaging apparatus in a desired manner. The securing ring 4 is further secured to the housing 3 by tightening screws 6. Similarly, the securing ring 4 may be fitted over and secured alternatively by other fasteners or a circlip to the outer circumference of the beam-limiting cone 10 in the dental imaging apparatus. Still alternatively, it may be fitted over and secured by an elastic element (e.g., a rubber element) to the outer circumference of the beam-limiting cone 10 in the dental imaging apparatus.

As shown in FIGS. 4 and 7, the visible light source 12 and the light-reflecting plate 13 are provided inside the housing 3 in such a manner that the light-reflecting plate 13 is inclined at an angle α of 45° with respect to a longitudinal axis L of the light passage (which is also a central axis of the housing 3) in order to reflect visible light emitted from the visible light source 12 toward the light field viewing window 7. The light-reflecting plate 13 is made of a material allowing transmission of X-rays therethrough. The visible light source 12 is an LED lamp, which is a cold light source generating less heat.

As shown in FIG. 7, as a means for adjusting the beam-limiting member, a light field adjusting lever 15 is provided outside the housing 3. The beam-limiting member includes a beam-limiting plate 14 disposed within the housing 3 upstream of the light field viewing window 7. Visible light and X-rays pass through the beam-limiting plate 14 and reach the light field viewing window 7. In use, the rotary switches may be manipulated as actually needed to control the size and extent of a light field produced. After passing through the light field viewing window 7, visible light will create a circular light field. The beam-limiting plate 14 is made of a material not allowing the transmission of visible light and X-rays therethrough.

Figure 8A:
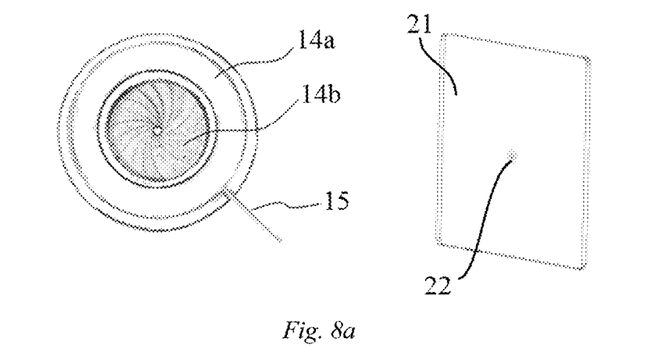
FIG. 8a schematically illustrates a beam-limiting plate in an externally-disposed circular collimator for a dental X-ray imaging apparatus according to the present application and a light field produced by light projected from the beam-limiting plate when it is in a closed state.
Figure 8B:
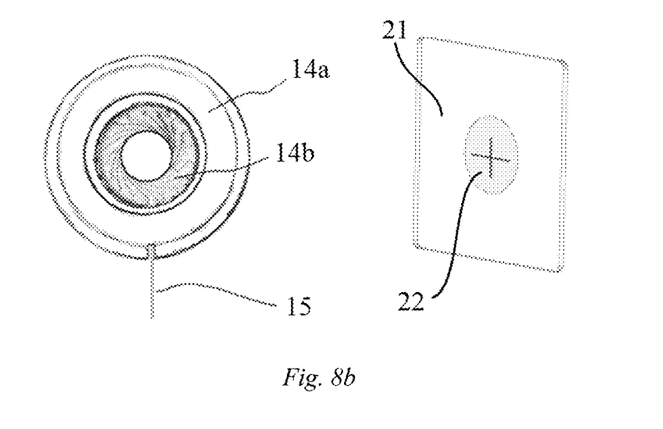
FIG. 8b schematically illustrates a beam-limiting plate in an externally-disposed circular collimator for a dental X-ray imaging apparatus according to the present application and a light field produced by light projected from the beam-limiting plate when it is in an open state.

As shown in FIGS. 8a and 8b, the beam-limiting plate 14 further includes a stationary portion 14a and a movable portion 14b. Movement of the movable portion 14b can be controlled by manipulating the light field adjusting lever 15. When the light field adjusting lever 15 is pivoted to the right, the movable portion 14b will displace outwardly from the stationary portion 14a, causing shrinkage of a light field 22 produced by light that has passed through the beam-limiting plate 14 and been projected onto a patient's face (mimicked with a projection target plate 21) (FIG. 8a). Pivoting the light field adjusting lever 15 to the left will cause expansion of a light field 22 produced by light that has passed through the beam-limiting plate 14 and been projected onto a patient's face (mimicked with a projection target plate 21) (FIG. 8b).

As shown in FIG. 5, on the same side of the housing 3 as the light field viewing window 7, an infrared sensing device 9 is disposed. When a hand of a person or a part of an object is present in an infrared sensing region, infrared radiation emitted from an infrared transmitter will be reflected by the person's hand or body onto an infrared receiver. After processing, a signal is issued and received by the lamp and instructs the lamp to emit light. After the person's hand or the object leaves the infrared sensing region, the lamp will not receive any signal and therefore will not emit light. The infrared sensing region reaches 20 cm ahead, and the signal lasts for 30 seconds. After the signal disappears, another signal may be issued when another sensing event happens.

Embodiment 3

A method of using an externally-disposed collimator for a dental X-ray imaging apparatus includes the steps of:
(Step 1) securing the externally-disposed collimator to an outer circumference of a beam-limiting cone in the dental imaging apparatus;
(Step 2) turning on a light source on the collimator to cause visible light to be emitted from an exit of the beam-limiting cone in the dental imaging apparatus;
(Step 3) determining an area for dental imaging and a projection direction for X-rays by adjusting the shape and size of a light field produced by the visible light and a position and angle of the beam-limiting cone in the dental imaging apparatus; and
(Step 4) activating the dental imaging apparatus, carrying out X-ray exposure, removing a dental film from a patient's mouth and ending the imaging process.

In some embodiments, the collimator is internally disposed at the bottom of the beam-limiting cone. In these cases, possible forms of the collimator also include square and circular collimators. A square collimator is able to produce square or rectangular visible light and X-ray fields with an adjustable size. A circular collimator is able to produce circular visible light and X-ray field with an adjustable size. The adjustable sizes make the apparatus suitable to be used with films of various sizes. Embodiments of these two collimator forms will be described below.

Embodiment 4

Figure 9:
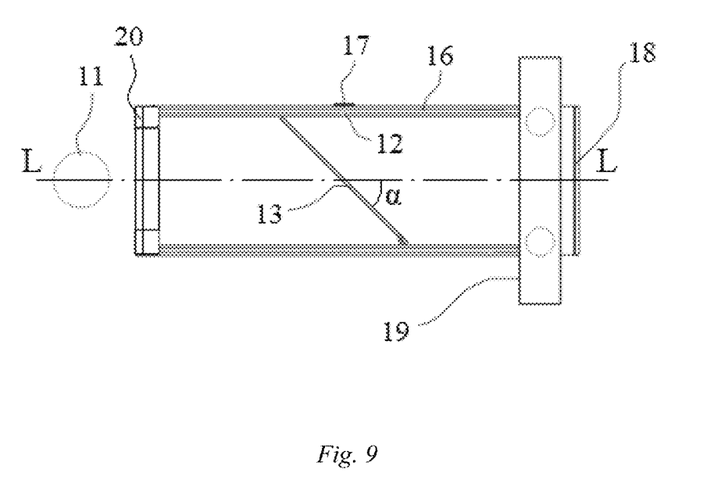
FIG. 9 schematically illustrates the internal structure of an internally-disposed square collimator for a dental X-ray imaging apparatus according to the present application.

As shown in FIG. 9, an internally-disposed square collimator for a dental X-ray imaging apparatus includes a housing, a securing means, a visible light source 12, a window member, a light-reflecting plate 13 and a beam-limiting member. In this embodiment, the housing includes a light projection casing 16, which has a light exit end and is secured to the dental X-ray imaging apparatus so as to define a light passage. X-rays emitted from the dental X-ray imaging apparatus travel through the light passage and exits from the light exit end. The beam-limiting member is disposed within a collimation casing 19 together with an associated adjustment member.

The visible light source 12 is arranged on an inner side wall of the light projection casing 16, and the light-reflecting plate 13 is disposed in the light projection casing 16 in such a manner that it is inclined at an angle α of 45° with respect to a longitudinal axis L of the light passage (which is also a central axis of the light projection casing 16) in order to reflect visible light toward a light exit aperture of a beam-limiting cone 10 in the dental imaging apparatus. X-rays are emitted from an X-ray source 11 toward the light exit aperture in the same direction as the visible light. The collimation casing 19 is disposed at the light exit end of the light projection casing 16 and is used to block undesired parts of the X-rays and visible light. The light-reflecting plate 13 is made of a material transmissive to X-rays.

The visible light source 12 is an LED lamp, which is a cold light source generating less heat. The visible light source 12 can be activated by manipulating a light source switch 17 on the light projection casing 16.

Figure 10:
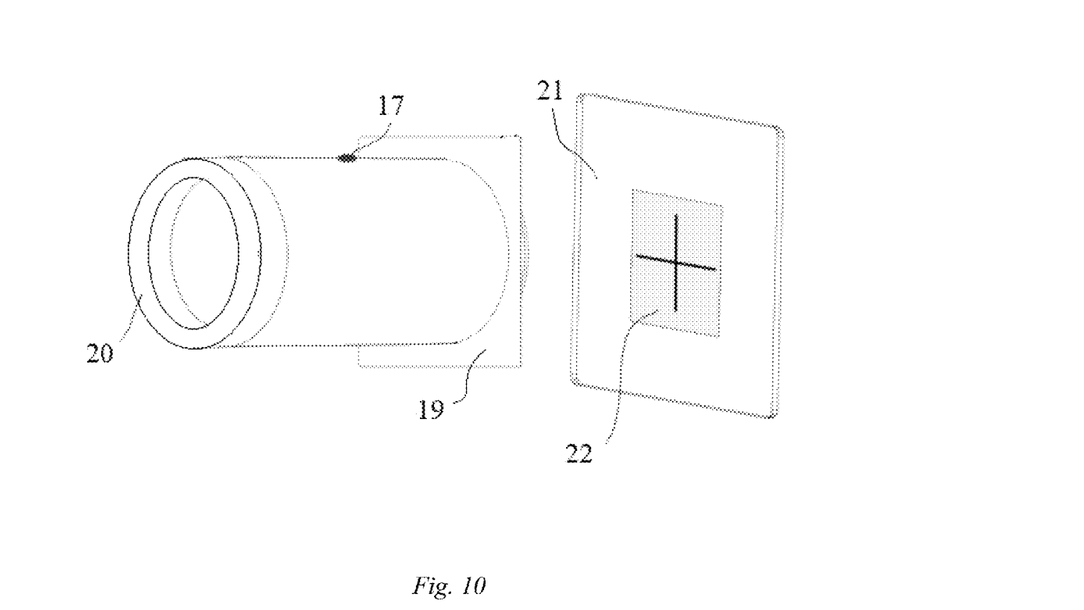
FIG. 10 schematically illustrates an imaging operation performed by an internally-disposed square collimator for a dental X-ray imaging apparatus according to the present application.
Figure 12:
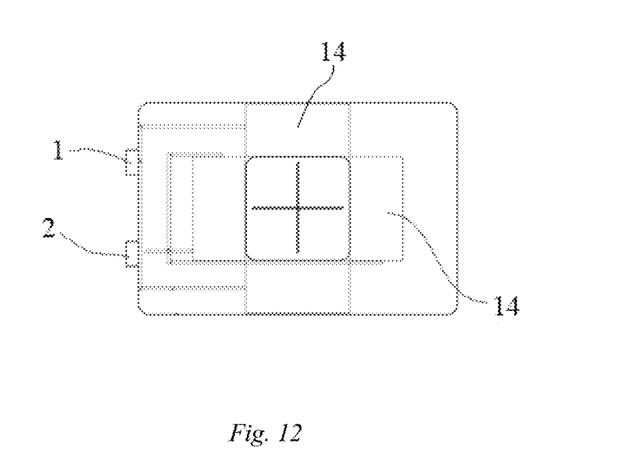
FIG. 12 is a schematic diagram illustrating the structure of a collimation casing in an internally-disposed square collimator for a dental X-ray imaging apparatus according to the present application.

As shown in FIG. 12, the collimation casing 19 is square and provided therein with the beam-limiting member and the associated adjustment member. The adjustment member includes an up-down light field adjustment rotary switch 1 and a left-right light field adjustment rotary switch 2, and the beam-limiting member includes four beam-limiting plates 14. The up-down light field adjustment rotary switch 1 is used to control movement of upper and lower beam-limiting plates 14, and the left-right light field adjustment rotary switch 2 is used to control movement of left and right beam-limiting plates 14. The beam-limiting plates 14 are made of a material opaque to X-rays. As shown in FIG. 10, in use, the rotary switches may be manipulated as actually needed to control the size and extent of a square light field 22 produced on a patient's face (mimicked with a projection target plate 21) by light projected from the square collimation casing 19.

Figure 11:
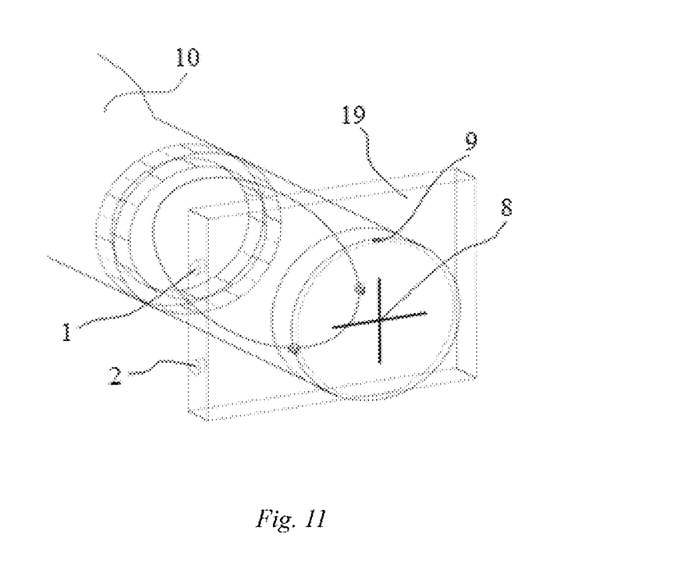
FIG. 11 is a schematic perspective view of an internally-disposed square collimator for a dental X-ray imaging apparatus according to the present application.

As shown in FIGS. 9 to 11, a transparent cover 18 is provided at the light exit end of the light projection casing 16 as the window member. The transparent cover 18 is provided thereon with a crosshair 8 serving as a light-shading mark for indicating a center of a light field created by projected light. After passing through the crosshair 8, visible light will create a light field with a cross-shaped shadow on the projection target plate 21.

As shown in FIG. 11, the light projection casing 16 is cylindrical and has a radius that is smaller than an inner radius of the commercial available beam-limiting cone 10 in the dental imaging apparatus. Thus, the light projection casing 16 can be received in the beam-limiting cone 10 of the dental imaging apparatus. Generally, a recess is defined by the light exit aperture at the bottom of the beam-limiting cone 10 in the dental imaging apparatus, and the collimator may be attractively retained at the bottom of the beam-limiting cone 10 in the dental imaging apparatus using a magnetically attractive member 20 (see FIGS. 9 and 10).

The collimator is further provided with an infrared sensing device 9. When a hand of a person or a part of an object is present in an infrared sensing region, infrared radiation emitted from an infrared transmitter will be reflected by the person's hand or body onto an infrared receiver. After processing, a signal is issued and received by the lamp and instructs the lamp to emit light. After the person's hand or the object leaves the infrared sensing region, the lamp will not receive any signal and therefore will not emit light. The infrared sensing region reaches 20 cm ahead, and the signal lasts for 30 seconds. After the signal disappears, another signal may be issued when another sensing event happens.

Embodiment 5

Figure 13:
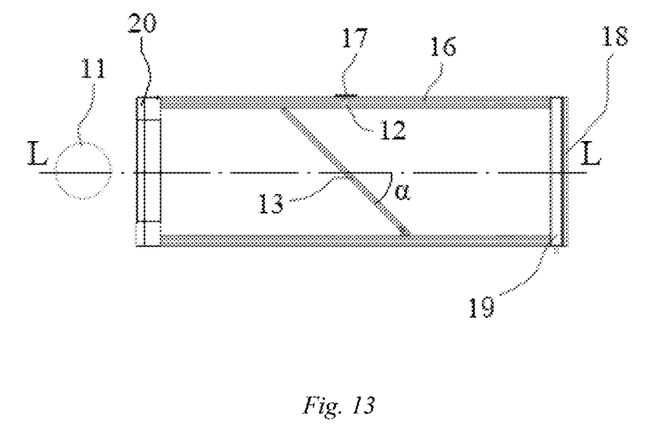
FIG. 13 schematically illustrates the internal structure of an internally-disposed circular collimator for a dental X-ray imaging apparatus according to the present application.

As shown in FIG. 13, an internally-disposed circular collimator for a dental X-ray imaging apparatus includes a housing, a securing means, a visible light source 12, a window member, a light-reflecting plate 13 and a beam-limiting member. In this embodiment, the housing includes a light projection casing 16, which has a light exit end and is secured to the dental X-ray imaging apparatus so as to define a light passage. X-rays emitted from the dental X-ray imaging apparatus travel through the light passage and exits from the light exit end. The beam-limiting member is disposed within a collimation casing 19 together with an associated adjustment member.

The visible light source 12 is arranged on an inner side wall of the light projection casing 16, and the light-reflecting plate 13 is disposed in the light projection casing 16 in such a manner that it is inclined at an angle α of 45° with respect to a longitudinal axis L of the light passage (which is also a central axis of the light projection casing 16) in order to reflect visible light toward a light exit aperture of a beam-limiting cone 10 in the dental imaging apparatus. X-rays are emitted from an X-ray source 11 toward the light exit aperture in the same direction as the visible light. The collimation casing 19 is disposed at the light exit end of the light projection casing 16 and is used to block undesired parts of the X-rays and visible light. The light-reflecting plate 13 is made of a material transmissive to X-rays.

The visible light source 12 is an LED lamp, which is a cold light source generating less heat. The visible light source 12 can be activated by manipulating a light source switch 17 on the light projection casing 16.

Figure 14:
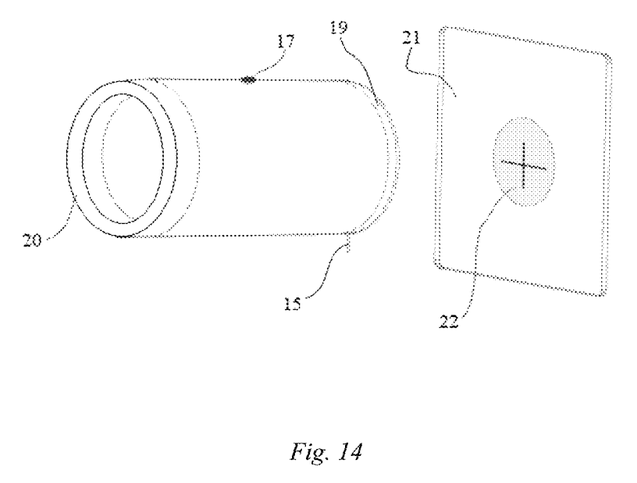
FIG. 14 schematically illustrates an imaging operation performed by an internally-disposed circular collimator for a dental X-ray imaging apparatus according to the present application.
Figure 16:
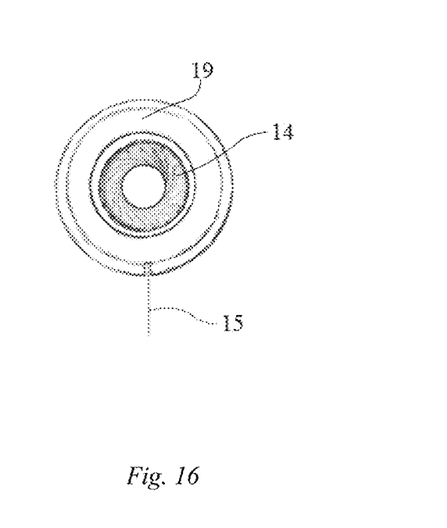

As shown in FIG. 16, the collimation casing 19 is circular and provided therein with the beam-limiting member and the associated adjustment member. The adjustment member includes a light field adjusting lever 15, and the beam-limiting member includes a beam-limiting plate 14. Movement of the beam-limiting plate 14 can be controlled by manipulating the light field adjusting lever 15. The beam-limiting plate 14 is made of a material opaque to X-rays. As shown in FIG. 14, in use, the light field adjusting lever 15 may be manipulated as actually needed to control the size and extent of a circular light field 22 produced on a patient's face (mimicked with a projection target plate 21) by light projected from the circular collimation casing 19.

Figure 15:
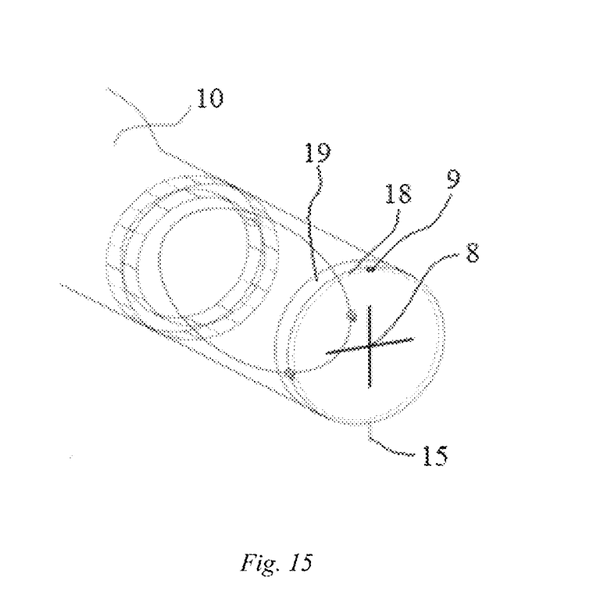
FIG. 15 is a schematic perspective view of an internally-disposed circular collimator for a dental X-ray imaging apparatus according to the present application.

As shown in FIGS. 13 to 15, a transparent cover 18 is provided at the light exit end of the light projection casing 16 as the window member. The transparent cover 18 is provided thereon with a crosshair 8 serving as a light-shading mark for indicating a center of a light field created by projected light. After passing through the crosshair 8, visible light will create a light field with a cross-shaped shadow on the projection target plate 21.

As shown in FIG. 11, the light projection casing 16 is cylindrical and has a radius that is smaller than an inner radius of the commercial available beam-limiting cone 10 in the dental imaging apparatus. Thus, the collimator can be received in the beam-limiting cone 10 of the dental imaging apparatus. Generally, a recess is defined by the light exit aperture at the bottom of the beam-limiting cone 6, and the collimator may be attractively retained at the bottom of the beam-limiting cone 10 in the dental imaging apparatus using a magnetically attractive member 20 (see FIGS. 13 and 14).

The collimator is further provided with an infrared sensing device 9. When a hand of a person or a part of an object is present in an infrared sensing region, infrared radiation emitted from an infrared transmitter will be reflected by the person's hand or body onto an infrared receiver. After processing, a signal is issued and received by the lamp and instructs the lamp to emit light. After the person's hand or the object leaves the infrared sensing region, the lamp will not receive any signal and therefore will not emit light. The infrared sensing region reaches 20 cm ahead, and the signal lasts for 30 seconds. After the signal disappears, another signal may be issued when another sensing event happens.

Embodiment 6

A method of using an internally-disposed collimator for a dental X-ray imaging apparatus includes the steps of:
(Step 1) placing the internally-disposed collimator inside a beam-limiting cone 10 in the dental imaging apparatus;
(Step 2) activating a light source switch 17 on the collimator to cause visible light to be emitted from an exit of the beam-limiting cone in the dental imaging apparatus;
(Step 3) determining an area for dental imaging and a projection direction for X-rays by adjusting the shape and size of a light field produced by the visible light and a position and angle of the beam-limiting cone 10 in the dental imaging apparatus; and
(Step 4) activating the dental imaging apparatus, carrying out X-ray exposure, removing a dental film from a patient's mouth and ending the imaging process.

The present invention rationally supplements the conventional projection techniques in terms of clinical practice, scientific research and education. It integrates visible light and X-ray fields and allows the extent and size of them to be adjusted in synchronization. Moreover, it allows a radiation field and its size to be adjusted. Thus, it has good utility effects.

Preferred specific embodiments have been described in detail above. It is to be understood that, those of ordinary skill in the art, without the need for creative effort, can make various modifications and changes, based on the concept of the present invention. Accordingly, all the technical solutions that can be obtained by those skilled in the art by logical analysis, inference or limited experimentation in accordance with the concept of the invention on the basis of the prior art are intended to fall within the protection scope as defined by the claims.

The invention claimed is:

1. A collimator for a dental X-ray imaging apparatus, comprising:
   a housing having a first end and a second end, which oppose each other, the first end of the housing provided thereat with a light exit aperture, the second end of the housing secured to the dental X-ray imaging apparatus so as to define a light passage so that X-rays emitted from the dental X-ray imaging apparatus are able to travel through the light passage and exit from the light exit aperture;
   a securing means disposed at the second end of the housing, with which the housing is detachably secured to a beam-limiting cone in the dental X-ray imaging apparatus;
   a visible light source placed within the housing and configured to be able to emit visible light;
   a window member disposed at the first end of the housing and configured to allow visible light and X-rays to transmit therethrough and be projected and irradiated onto an object to be imaged;
   a light-reflecting plate placed in the housing obliquely with respect to a longitudinal axis of the light passage and configured to be able to reflect visible light emitted from the visible light source so that the reflected visible light is able to pass through the window member and be projected on the object to be imaged;
   a beam-limiting member disposed between the light-reflecting plate and the window member and configured to disallow transmission of visible light and X-rays therethrough and hence define the light exit aperture.

2. The collimator for a dental X-ray imaging apparatus according to claim 1, wherein the visible light source is positioned on an inner wall of the housing.

3. The collimator for a dental X-ray imaging apparatus according to claim 1, wherein the window member is provided at a center thereof with a light-shading mark for indicating an area on which the visible light is projected.

4. The collimator for a dental X-ray imaging apparatus according to claim 1, wherein the light-reflecting plate is made of a material transmissive to X-rays.

5. The collimator for a dental X-ray imaging apparatus according to claim 1, wherein the light-reflecting plate forms an angle of 45° with the longitudinal axis of the light passage.

6. The collimator for a dental X-ray imaging apparatus according to claim 5, wherein a position of a virtual image of the visible light source formed by the light-reflecting plate coincides with a position of an X-ray source in the dental X-ray imaging apparatus in a direction along the longitudinal axis of the light passage.

7. The collimator for a dental X-ray imaging apparatus according to claim 1, further comprising an adjustment member disposed on the housing and configured to be able to change a size and/or a shape of the light exit aperture defined by the beam-limiting member.

8. The collimator for a dental X-ray imaging apparatus according to claim 1, wherein the visible light source is an LED lamp.

9. The collimator for a dental X-ray imaging apparatus according to claim 1, wherein the securing means is configured to be able to be fitted over and thereby connected to an outer circumference of the beam-limiting cone in the dental X-ray imaging apparatus.

10. The collimator for a dental X-ray imaging apparatus according to claim 1, wherein the securing means is configured to be able to be connected to a bottom of the beam-limiting cone in the dental X-ray imaging apparatus by magnetic attraction.

11. The collimator for a dental X-ray imaging apparatus according to claim 7, wherein the beam-limiting member further comprises a set of first beam-limiting blocks and a set of second beam-limiting blocks, which are arranged orthogonally to each other, the set of first beam-limiting blocks including a pair of first beam-limiting blocks in opposition to each other, and the set of second beam-limiting blocks including a pair of second beam-limiting blocks in opposition to each other, and wherein the adjustment member is configured to control the pair of first beam-limiting blocks to move relative to each other and to control the pair of second beam-limiting blocks to move relative to each other.

12. The collimator for a dental X-ray imaging apparatus according to claim 7, wherein the beam-limiting member further comprises a stationary portion and a movable portion, the stationary portion configured as an annulus, the movable portion comprising a plurality of beam-limiting blocks, each of the plurality of beam-limiting blocks pivotably coupled to the stationary portion and evenly distributed around a center of the stationary portion, and wherein the adjustment member is configured to switch the plurality of beam-limiting blocks between a closed state and an open state.

13. The collimator for a dental X-ray imaging apparatus according to claim 1, wherein the housing is further provided thereon with a switch for activating or deactivating the visible light source.

14. The collimator for a dental X-ray imaging apparatus according to claim 1, wherein the housing is further provided thereon with an infrared sensing device configured to sense the object to be imaged and responsively activate or deactivate the visible light source.

15. A dental X-ray imaging apparatus, comprising:
an X-ray source;
a body for housing the X-ray source;
a beam-limiting cone disposed externally around the X-ray source and extending out of the body;
a collimator comprising: a housing having a first end and a second end, which oppose each other, the first end of the housing provided thereat with a light exit aperture, the second end of the housing secured to the beam-limiting cone so as to define a light passage so that X-rays emitted from the dental X-ray imaging apparatus are able to travel through the light passage and exit from the light exit aperture; a securing means disposed at the second end of the housing, with which the housing is detachably secured to the beam-limiting cone; a visible light source placed within the housing and configured to be able to emit visible light; a window member disposed at the first end of the housing and configured to allow visible light and X-rays to transmit therethrough and be projected and irradiated onto an object to be imaged; a light-reflecting plate placed in the housing obliquely with respect to a longitudinal axis of the light passage and configured to be able to reflect visible light emitted from the visible light source so that the reflected visible light is able to pass through the window member and be projected on the object to be imaged; a beam-limiting member disposed between the light-reflecting plate and the window member and configured to disallow transmission of visible light and X-rays therethrough and hence define the light exit aperture.

16. The dental X-ray imaging apparatus according to claim 15, wherein the light-reflecting plate forms an angle of 45° with the longitudinal axis of the light passage.

17. The dental X-ray imaging apparatus according to claim 16, wherein a position of a virtual image of the visible light source formed by the light-reflecting plate coincides with a position of the X-ray source in the dental x-ray imaging apparatus in a direction along the longitudinal axis of the light passage.

18. The dental X-ray imaging apparatus according to claim 15, wherein the beam-limiting member further comprises an adjustment member disposed on the housing and configured to change a size and/or a shape of the light exit aperture defined by the beam-limiting member.

19. The dental X-ray imaging apparatus according to claim 18, wherein the beam-limiting member further comprises a set of first beam-limiting blocks and a set of second beam-limiting blocks, which are arranged orthogonally to each other, the set of first beam-limiting blocks including a pair of first beam-limiting blocks in opposition to each other, and the set of second beam-limiting blocks including a pair of second beam-limiting blocks in opposition to each other, and wherein the adjustment member is configured to control the pair of first beam-limiting blocks to move relative to each other and to control the pair of second beam-limiting blocks to move relative to each other.

20. The dental X-ray imaging apparatus according to claim 18, wherein the beam-limiting member further comprises a stationary portion and a movable portion, the stationary portion configured as an annulus, the movable portion comprising a plurality of beam-limiting blocks, each of the plurality of beam-limiting blocks pivotably coupled to the stationary portion and evenly distributed around a center of the stationary portion, and wherein the adjustment member is configured to switch the plurality of beam-limiting blocks between a closed state and an open state.

* * * * *